United States Patent [19]

Matthias

[11] 4,176,410
[45] Dec. 4, 1979

[54] SPORT GOGGLE

[75] Inventor: Jan H. Matthias, Greispinzgau, Austria

[73] Assignee: Carrera International Corporation, Norwood, N.J.

[21] Appl. No.: 912,023

[22] Filed: Jun. 2, 1978

[30] Foreign Application Priority Data

Jun. 3, 1977 [DE] Fed. Rep. of Germany ... 7716671[U]

[51] Int. Cl.² .............................................. A61F 9/02
[52] U.S. Cl. ........................................ 2/436; 2/452; 2/454; 2/439
[58] Field of Search ................... 2/436, 454, 437, 439, 2/447, 452

[56] References Cited

U.S. PATENT DOCUMENTS

| | | | |
|---|---|---|---|
| 2,618,782 | 11/1952 | Christensen et al. | 2/436 |
| 2,907,041 | 10/1959 | Finn | 2/454 X |
| 3,591,864 | 7/1971 | Allsop | 2/436 |
| 3,945,044 | 3/1976 | McGee et al. | 2/436 |

Primary Examiner—Peter Nerbun
Attorney, Agent, or Firm—Fitch, Even & Tabin

[57] ABSTRACT

A sport goggle is disclosed which includes a rectangular flexible frame normally disposed in planar relation and bendable to conform to a wearer's head on which the goggle may be secured by flexible straps secured to opposite ends of the frame. The frame supports a removable rectangular lens and has a face engaging cushion spaced from the lens by support pads which define air vents therebetween over which flexible air filters are mounted. The straps are adapted to be folded about and secured to the frame so as to protect the lens during non-use.

13 Claims, 8 Drawing Figures

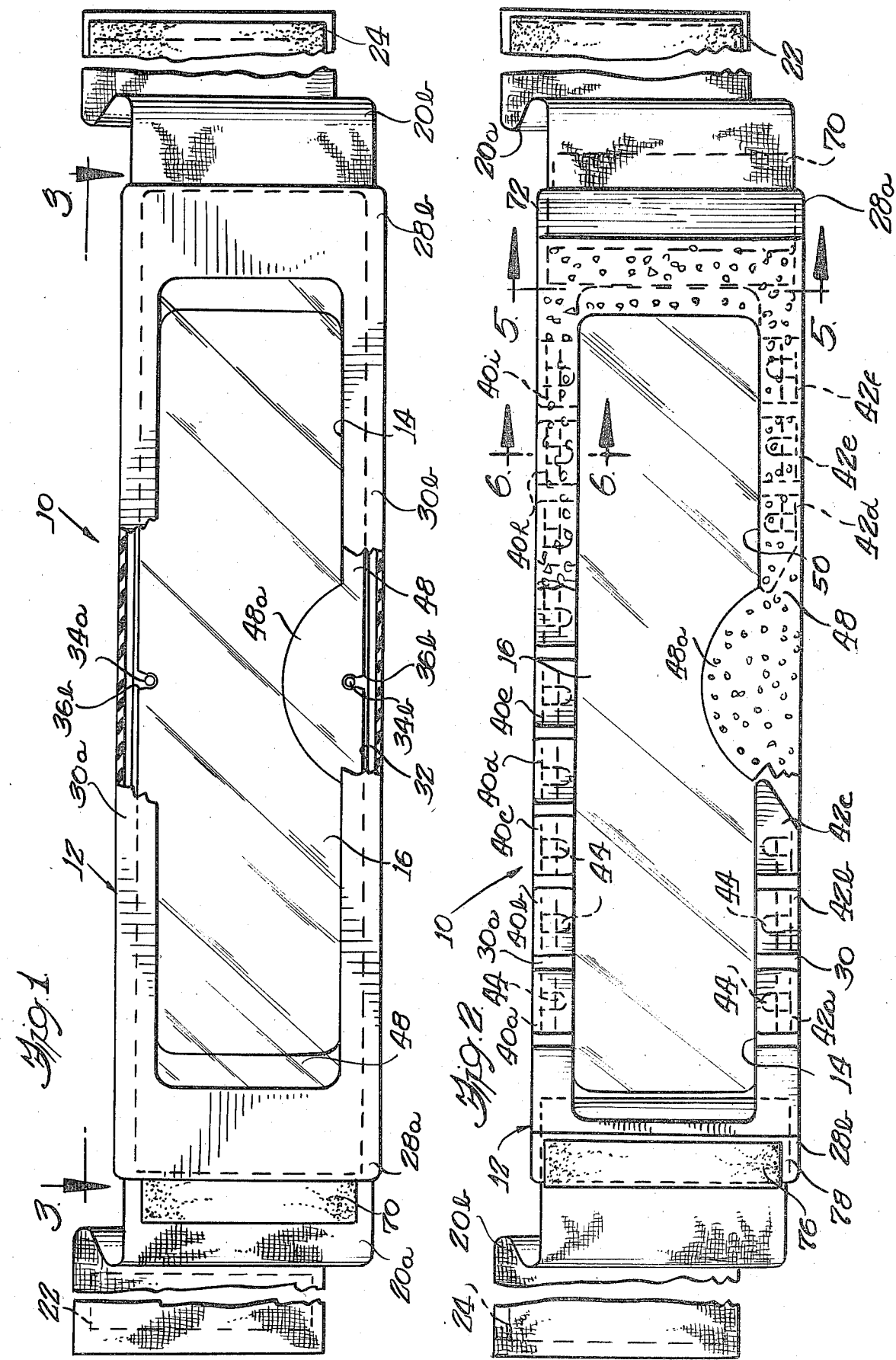

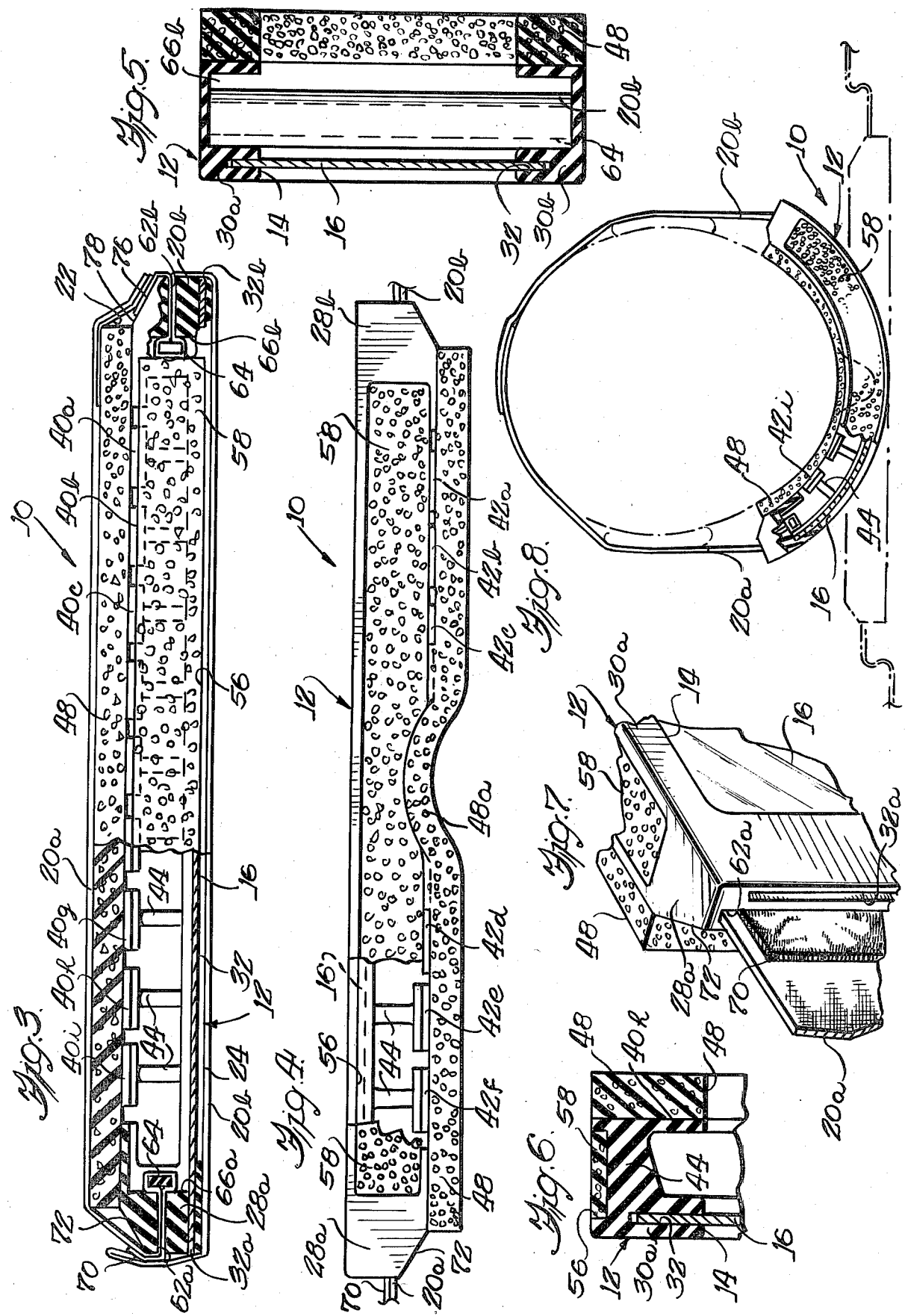

SPORT GOGGLE

The present invention relates generally to goggles, and more particularly to a novel sport goggle which includes a flexible rectangular frame bendable from a planar condition to conform to a wearer's head so as to provide substantially universal sizing, the frame having flexible straps secured to its opposite ends which facilitate mounting on the wearer's head and which, when the goggle is not in use, may be folded to overlie the lens and provide protection therefor.

It is a common practice in many sporting activities, such as skiing, cycling, road racing and the like to wear protective goggles which serve to protect the eyes from wind and undesirable foreign particles. It is desirable that such goggles have lenses which may be quite easily removed and replaced, and also that they be adapted to ventilate the area rearwardly of the lens while the goggle is being worn so as to prevent fogging.

A number of significant drawbacks exist in the known prior art sport goggles, including the failure of a single goggle design to provide substantially uniform fit over a wide range of head sizes, thereby requiring a range of production sizes each of which will comfortably fit a relatively small range of different wearer head sizes. Additionally, the known goggle lens support frames, in the majority, are pre-contoured so as to conform generally to the human facial structure. Preforming the frames to predetermined contours reduces the adaptability of a goggle for wear by persons having different facial contours and sizes. The pre-contoured goggles also make stacking of a plurality of similarly shaped goggles for shipping and storage difficult. Still further, the known goggle designs fail to adequately protect the associated lenses from scratching and possible fracture during normal handling. There thus exists a need for a goggle which provides substantially universal fit for different head sizes and shapes, which facilitates generally flat stacking of a plurality of the goggles during shipping and storage, and which further provides for protection of the associated lens without requiring separate packaging.

One of the primary objects of the present invention is to provide a novel goggle which provides a substantially universal fit whereby to readily accommodate different head sizes.

A more particular object of the present invention is to provide a novel goggle having a generally rectangular flexible lens supporting frame having flexible straps secured to opposite ends thereof to facilitate mounting of the goggle on a wearer's head, which straps may be secured to the frame during nonuse in a manner to protect the lens from scratches and the like.

A feature of the goggle in accordance with the present invention lies in the provision of a rectangular flexible lens supporting frame which has a substantially planar configuration when not being worn and which may be readily bent or flexed to conform to a wearer's head on which the goggle may be secured by flexible straps secured to opposite ends of the frame.

An additional feature of the goggle of the present invention lies in the provision of flexible straps secured to opposite ends of the rectangular frame and having free ends cooperable with means adjacent the opposite ends of the frame so as to secure the straps in folded overlying relation forwardly and rearwardly of the lens in protective relation therewith.

Another feature of the goggle in accordance with the present invention lies in the provision of novel support pads on the frame which serve to support a resilient cushion for direct engagement with the wearer's face, the pads defining air ventilation passages therebetween and being supported so as to readily accommodate movement of the frame between planar and curved conditions.

Further objects and advantages of the present invention, together with the organization and manner of operation thereof, will become apparent from the following detailed description of the invention when taken in connection with the accompanying drawings wherein like reference numerals designate like elements throughout the several views, and wherein:

FIG. 1 is a front elevational view of a goggle constructed in accordance with the present invention, portions being broken away for clarity;

FIG. 2 is a rear elevational view of the goggle of FIG. 1, with portions being broken away for clarity;

FIG. 3 is a top plan view taken substantially along line 3—3 of FIG. 1, but showing the straps folded into protective relation with the lens and with portions broken away for clarity;

FIG. 4 is a bottom view of the goggle of FIG. 1, but with portions being broken away for clarity;

FIG. 5 is a fragmentary transverse sectional view, on an enlarged scale, taken substantially along line 5—5 of FIG. 2, looking in the direction of the arrows;

FIG. 6 is a transverse sectional view taken along line 6—6 of FIG. 2, looking in the direction of the arrows;

FIG. 7 is a fragmentary perspective view of the left-hand end of the goggle, as viewed in FIG. 1; and FIG. 8 is a plan view illustrating the goggle in a curved condition as during use.

Referring now to the drawings, and in particular to FIGS. 1-4, a goggle constructed in accordance with a preferred embodiment of the present invention is indicated generally at 10. The goggle 10, which may alternatively be termed a sport goggle, is particularly suitable for use in sporting activities such as skiing, cycling, auto road racing and the like, or other activities where it is desirable that a goggle be worn to protect the eyes from the wind and foreign particles which could cause damage to the eyes or otherwise impair one's vision. The goggle 10 may have a tinted lens so as to also provide a desired visual effect and protect the wearer's eyes from glare and ultraviolet rays from the sun.

Very generally, the goggle 10 includes a rectangularly shaped flexible frame 12 which, when not being worn, has a generally planar configuration as shown in FIG. 3 and which is bendable about an axis generally transverse to its major longitudinal axis to conform to the wearer's head when being worn. The frame 12 is of sufficient longitudinal length so as to extend across the wearer's face proximate the wearer's eyes and has a rectangular opening 14 centrally of the frame in which is mounted a rectangular lens 16. The opening 14 and associated lens 16 are of sufficient area to permit viewing therethrough by both of the wearer's eyes when the goggle is worn so that a wide field of vision is provided.

A pair of flexible straps 20a and 20b are secured to the opposite ends of the frame 12 so as to extend coaxially with the longitudinal axis of the frame. The straps have mutually cooperable adhesive type securing means on their outer ends, indicated at 22 and 24, respectively, which facilitate attachment of the free ends of the straps around the wearer's head at a desired tightness. As will become more apparent hereinbelow, the straps 20a, b are of sufficient length and transverse width to overlie the opening 14 and the exposed inner and outer surfaces of the lens 16 when the straps are folded one forwardly and one rearwardly, about the frame so as to provide protection to the lens. Means are located at each end of the frame for cooperation with the free end of the strap attached to the opposite frame end so as to releasably retain the straps in folded lens protecting positions during nonuse of the lens.

Turning now to a more detailed description of the goggle 10, the frame 12 is preferably made of a resilient flexible material such as a suitable plastic or rubber which may be mold formed to define opposite ends 28a and 28b integrally interconnected through upper and lower frame edge portions or rails 30a and 30b. The rails 30a, b cooperate with the ends 28a, b to form the perimeter of the opening 14. The frame 12 is formed with a continuous lens receiving slot 32 which extends through the full longitudinal length of the frame and intersects the opposite ends 28a, b as at 32a, 32b, respectively. The slot 32 is disposed parallel to and slightly rearwardly of the forward surface of the frame 12 and is adapted to receive the rectangular shaped lens 16 so as to facilitate entry of the lens into the slot from either end 32a or 32b of the slot 32.

As best seen in FIG. 1, at least one and preferably a pair of locating nibs 34a and 34b are formed integral with the upper and lower frame edge portions 30a, b, respectively, so as to transverse the associated slot 32. The nibs 34a, b are adapted for registration with suitably configured recesses 36a and 36b formed in the longitudinal edges of the lens 16. The nibs 34a, b and lens recesses 36a, b are preferably located at the longitudinal centers of the frame and lens, respectively, so that the lens may be inserted within the slot 32 and moved to a predetermined position wherein the nibs are received within the lens recesses without concern for a particular "upper" or "lower" edge orientation of the lens relative to the frame. The lens has a longitudinal length sufficient to extend the full longitudinal length of the slot 32 when inserted therein.

The frame 12 has a plurality of support or mounting pads 40a-i formed integral along the length of the upper frame edge 30a so that the rearwardly or outwardly facing surfaces of the support pads lie coplanar with the rearwardly facing surfaces of the frame end portions 28a, b. Similar supporting pads 42a-f are formed integral with the lower frame edge 30b so that their rearwardly facing surfaces are coplanar with the rearwardly facing surfaces of the support pads 40a-i and frame ends 20a, b. Each of the support pads 40a-i and 42a-f are integrally supported on their respective upper and lower frame edges 30a, b through identical associated flexible posts 44 so that the support pads are spaced rearwardly from the frame edges 30a, b and are spaced longitudinally along the frame edges so as to define air ventilation openings therebetween along the full lengths of the upper and lower edges of the frame.

The support pads 40a-i and 42a-f cooperate with the rearwardly facing surfaces of the frame ends 28a, b to provide supporting surfaces to which a flexible resilient sponge-like cushion 48 is attached as by a suitable adhesive. The cushion 48 has a generally rectangular configuration having a rectangular central opening 50 corresponding substantially in size to the opening 14 in the frame 12. The cushion 48 provides a resilient surface for direct contact with the wearer's face to provide a comfortable interface between the goggle frame and wearer's face.

As best seen in FIGS. 2 and 4, the support pads 42c and 42d on the lower edge 30b of the goggle frame are spaced apart a distance greater than the spacing between the remaining support pads to define an unobstructed area adjacent the bottom edge of the frame corresponding to the area of the wearer's nose when the goggle is mounted on the wearer's face. Preferably, the cushion 48 is contoured at 48a in the area of the wearer's nose so as to provide a comfortable cushioning with the wearer's nose.

The rearwardly facing edges of the upper and lower longitudinal frame edges 30a and 30b are recessed at 56, as best seen in FIG. 6, to receive strips of foraminous flexible filter material 58 which may be similar to the sponge-like material forming the cushion 48. The filter strips 58 permit air passage through the ventilation openings defined between the various support pads 40a-i and 42a-f while preventing entry of undesirable foreign matter or particles. The filter strips 58 are preferably adhesively secured along their longitudinal edges to the rearward edges of the frame rails 30a, b and to oppositely facing surfaces of the associated mounting pads 40a-i and 42a-f, and are of sufficient resiliency to accommodate bending of the frame when mounted on the wearer's head without adversely affecting the filtering characteristics of the filter strips.

The straps 20a and 20b are made of suitable strength fabric material having interwoven elastic filaments therein which permit elastic longitudinal elongation of the straps while inhibiting elastic expansion of the bands in directions transverse to their longitudinal lengths. With particular reference to FIGS. 3 and 5, each of the straps 20a, b has its inner end received through a slot 62a, b respectively, formed in the opposite ends 28a, b of the frame 12. The inner end of each of the straps 20a, b is looped about a transverse rod 64 and abuts a corresponding transverse surface 66a or 66b formed on the opposite ends 28a, b of the frame so as to prevent withdrawal of the straps from their associated slots 62a, b. Preferably, the transverse surfaces 62a, b are located so that the looped inner ends of the straps are not visible from the front of the goggle 10.

As mentioned, the outer ends of the straps 20a, b have mutually cooperable adhesive type securing or fastening means thereon which facilitate releasable connection of the juxtaposed end of the straps when wrapped around the wearer's head with the frame 12 conforming to the wearer's face. One of the adhesive pads or areas, such as 24, comprises a multiplicity of small filamentary elements having curled outer ends, while the other area 22 comprises a multiplicity of filamentary loops adapted when pressed against the filament area 24 to releasably adhere thereto. Such fasteners are commercially available as Velcro type fasteners. In this manner, the straps 20a, b may be wrapped about the wearer'head to a desired tightness and the outer ends of the straps interconnected to maintain the goggle in a desired position.

The inner end of strap 20a has an adhesive area 70 formed thereon adjacent the end 28a of the frame so that when strap 20a is wrapped rearwardly of the goggle as in FIG. 3, the adhesive area 70 faces outwardly from the end surface of the frame end 28a and may overlie a rearwardly inclined surface 72 formed on the frame adjacent end 28a. The adhesive area 70 is adapted for attachment to the adhesive area 24 formed on the outer end of the opposite strap 20b when the strap 20b is wrapped around the frame 12 so as to overlie the front surface of the frame and the exposed forward surface of the lens 16 in protective relation therewith. Thus, if the adhesive area 24 defines a multiplicity of small filamentary elements having curled outer ends, the adhesive area 70 is made to define a multiplicity of small loop filaments which are releasably attachable to the curled filaments of the adhesive area 24.

The strap 20b also has a second adhesive area 76 formed thereon in the form of a flap secured at one edge to the inner end of the strap 20b and wrapped about the end 28b of the frame so as to lie against a rearwardly inclined surface 78 on the frame to which the flap 76 is adhesively secured. The outer exposed surface of flap 76 defines a multiplicity of looped filaments adapted for releasable attachment to the adhesive area 22 on the outer end of strap 20a so that when strap 20a is wrapped rearwardly of the frame and lens, its outer end may be releasably secured to the adhesive flap 76 at the opposite end 28b of frame 12.

Having thus described a preferred embodiment of the goggle 10 in accordance with the present invention, it is seen that the goggle provides a number of distinct features and advantages over the known prior art goggles. Among the various features and advantages is the unique rectangular configuration of the flexible frame 12 which has a substantially planar configuration when not being worn but which may be readily flexed about an axis generally transverse to its longitudinal axis so as to conform to the wearer's face and head. The support pads 40a-i and 42a-f maintain the forward portion of the frame and the associated lens in spaced relation from the wearer's face to facilitate air ventilation between the corresponding pad support posts 44 and provide support surfaces for the resilient cushion 48. The straps 20a and 20b have transverse widths approximately equal to the transverse dimension of the frame lens opening 14 so that the straps may be folded and secured forwardly and rearwardly of the frame to protect the lens during nonuse. By releasably securing the ends of the straps to the opposite ends of the frame 12, the straps maintain their lens protecting positions until manually released from the ends of the frame preparatory to mounting the goggle on the wearer's head. The unitary rectangular frame construction with the flexible support pads 40 and associated cushion 48 cooperate to provide a comfortable fit for any wearer's face and head independently of head size.

While a preferred embodiment of the goggle in accordance with the present invention has been illustrated and described, it will be understood to those skilled in the art that changes and modifications may be made therein without departing from the invention in its broader aspects.

Various features of the invention are defined in the following claims.

What is claimed is:

1. A goggle comprising a generally rectangular flexible frame having a normally planar configuration when not being worn and being bendable to conform to the wearer's head when worn, said frame being of sufficient longitudinal length to extend across the wearer's face proximate the wearer's eyes when worn and defining a substantially rectangular opening of sufficient area to permit viewing therethrough by both of the wearer's eyes, a lens mounted on said frame within said opening and having a peripheral edge surface fully engaged by said frame when mounted thereon with the lens covering substantially the full area of said opening, a pair of flexible straps each of which is secured to an opposite end of said frame so as to extend generally longitudinally therefrom, said straps having mutually cooperable securing means thereon facilitating attachment of the free ends of said straps together around the wearer's head at a desired tightness thereabout, said straps being of sufficient length and transverse width to overlie said opening when said straps are folded, one forwardly and one rearwardly, about said frame so as to protect the lens, and means located substantially at each end of said frame for cooperation with an end of the strap secured to the opposite frame end so as to releasably retain said straps in said folded lens protecting positions.

2. A goggle as defined in claim 1 wherein said frame has a slot extending therethrough so as to intersect the opposite ends of said frame and said opening in said frame, said lens being insertable within said slot from either end of said frame.

3. A goggle as defined in claim 2 wherein said frame has at least one locating nib formed thereon within said lens receiving slot, said lens having a recess therein adapted for registration with said locating nib when said lens is disposed in predetermined position within said slot relative to said frame.

4. A goggle as defined in claim 1 wherein said frame has upper and lower longitudinally extending portions each of which defines air ventilation openings therethrough to facilitate entry of air behind the lens when the goggle is worn so as to prevent fogging of the lens.

5. A goggle as defined in claim 4 including air filter means mounted in overlying relation to said ventilation openings so as to prevent entry of contaminants through said ventilation openings while allowing air flow therethrough.

6. A goggle as defined in claim 1 wherein said frame has a plurality of cushion support pads formed thereon along upper and lower longitudinal edge portions of said frame, said pads being spaced along said frame so as to define air ventilation openings therebetween without inhibiting bending of said frame about an axis substantially transverse to its longitudinal axis so as to conform to the contour of the wearer's head.

7. A goggle as defined in claim 6 including a resilient cushion mounted on said support pads for engagement with the wearer's face.

8. A goggle frame comprising a generally rectangular flexible frame having a normally planar configuration when not being worn but being bendable about an axis substantially transverse to the longitudinal axis of the frame to conform to a wearer's head when being worn, said frame being of sufficient longitudinal length to extend across the wearer's face proximate the wearer's eyes and defining a generally rectangular opening of sufficient area to permit viewing therethrough by both of the wearer's eyes when the goggle is worn, said frame being adapted to receive a lens in mounted relation thereon with the lens overlying said opening, a pair of flexible straps secured to the opposite ends of said frame so as to extend with the longitudinal axes of said straps substantially coaxial with the longitudinal axis of said frame, said straps having mutually cooperable means on their outer free ends facilitating releasable attachment of the free ends of the straps when wrapped about the wearer's head and to maintain the frame in mounted relation on the wearer's head, said frame having a plurality of discrete support pads thereon disposed in substantially coplanar relation with each other when said frame is in its said planar condition, said support pads being spaced from the lens supporting portion of said frame and defining a plurality of air ventilation openings therebetween, and a resilient cushion mounted on said support pads for engagement with the wearer's face when wearing said goggle frame.

9. A goggle as defined in either of claims 7 or 8 including flexible foraminous filter means supported on said frame so as to substantially overlie said air ventilation openings, said flexible filter means being adapted to accommodate bending of said frame to conform to the wearer's head.

10. A goggle as defined in either of claims 1 or 8 wherein said flexible straps are elastically extendible along their longitudinal lengths.

11. A goggle as defined in either of claims 1 or 8 wherein said mutually cooperable securing means on said straps comprise adhesive type securing means.

12. A goggle as defined in claim 11 wherein said mutually cooperable adhesive type securing means on said flexible straps comprises an area of small filamentary elements having curled outer ends formed adjacent the free end of one of said straps, the other of said straps having an area formed thereon adjacent its outer end consisting of a multiplicity of small filamentary loops, said filamentary elements and loops adjacent said outer ends of said straps being adapted for mutual interengagement when said straps are folded about a wearer's head when mounting said goggles thereon so as to releasably retain said straps in attached relation.

13. A goggle as defined in claim 11 wherein said means located at the opposite ends of said frame to releasably retain said straps in said folded lens protecting positions includes, on one end of the frame, an adhesive area adapted for releasable attachment with the adhesive area on the free end of the strap attached to the opposite end of said frame, and an adhesive area on the opposite end of said frame adapted for releasable attachment to the adhesive area on the free end of the other of said straps so as to permit wrapping and securing of said straps forwardly and rearwardly of said frame in overlying relation to said lens.

* * * * *